United States Patent [19]
Torii et al.

[11] Patent Number: 5,894,082
[45] Date of Patent: Apr. 13, 1999

[54] APPARATUS FOR MEASURING OXYGEN WITHIN MOLTEN SUBSTANCE

[75] Inventors: Toyohiko Torii; Tetsumi Murata, both of Tokyo; Keiichi Mori; Hisao Ikawa, both of Osaka, all of Japan

[73] Assignee: Kawaso Electric Industrial Co., Inc., Osaka, Japan

[21] Appl. No.: 08/859,048

[22] Filed: May 20, 1997

[51] Int. Cl.[6] .................................................. G01N 33/20
[52] U.S. Cl. .................... 73/19.07; 204/422; 204/424; 436/75; 436/138
[58] Field of Search .................. 73/19.07, 31.05, 73/DIG. 9; 204/421, 422, 424; 436/75, 138

[56] References Cited

U.S. PATENT DOCUMENTS

| | | | |
|---|---|---|---|
| 3,468,780 | 9/1969 | Fischer | 204/422 |
| 3,630,874 | 12/1971 | Olette et al. | 204/422 |
| 4,045,319 | 8/1977 | Deportes et al. | 204/422 |
| 4,313,799 | 2/1982 | Perkins | 204/422 X |
| 4,906,349 | 3/1990 | Beatrice et al. | 204/422 |
| 5,596,134 | 1/1997 | Phillippi et al. | 73/19.07 |

*Primary Examiner*—Daniel S. Larkin
*Attorney, Agent, or Firm*—Sixbey, Friedman, Leedom & Ferguson; David S. Safran

[57] ABSTRACT

An apparatus for measuring oxygen within a molten substance comprises a compact oxygen probe unit constructed by assembling a tubular shell whose one end is closed, which is made of solid electrolyte and which is to be soaked into the molten substance to be measured, a metal cylinder which surrounds the outer periphery of the shell and which serves also as an outer electrode and a sheath thermocouple which is inserted to a reference pole provided within an inner face of the shell and which serves also as an inner electrode to a terminal box. The metal cylinder comprises a protecting cylinder portion which surrounds the outer periphery of the shell and an opening for exposing the closed end of the shell. Both element wires of the sheath thermocouple are connected to temperature measuring means via the terminal box. The inner electrode formed by one element wire of the thermocouple and the outer electrode formed by the metal cylinder are connected to electromotive force measuring means also via the terminal box.

8 Claims, 4 Drawing Sheets

5,894,082

1

APPARATUS FOR MEASURING OXYGEN WITHIN MOLTEN SUBSTANCE

FIELD OF THE INVENTION

The present invention relates to an apparatus for continuously measuring an activity of oxygen within molten substance such as molten glass.

BACKGROUND OF THE INVENTION

It has been known that an activity of oxygen within molten glass in a glass manufacturing process largely affects color, ultraviolet absorptivity, and the like of the produced glass for example. Although an apparatus which allows the activity of oxygen within the molten glass to be continuously measured and its result to be reflected in the manufacturing process has been expected, it is the present state unfortunately that no such apparatus which meets with such expectation has been provided.

There has been known an apparatus for measuring an activity of oxygen within molten metal. Such apparatus comprises a tubular shell which is made of solid electrolyte such as zirconia, whose one end is closed and which is to be soaked into a molten substance to be measured, a reference pole which is provided at an inner face of the shell and which is made of a reference substance which gives a predetermined activity of oxygen, an inner electrode inserted to the reference pole, an outer electrode made of a metal rod to be soaked into the molten substance to be measured and a sheath thermocouple which is to be soaked into the molten substance to be measured to measure temperature of the molten substance.

In measuring the activity of oxygen within the molten metal by the known apparatus, the tubular shell, the outer electrode, and the sheath thermocouple are soaked into the molten metal, respectively. An oxygen concentration cell which generates electromotive force E(V) based on a difference of partial pressure of oxygen existing between the molten substance and the reference pole is formed between the outer and inner faces of the shell made of the solid electrolyte. This electromotive force E(V) is measured by electromotive force measuring means connected to the outer and inner electrodes. The temperature T(K) of the molten substance is measured by the sheath thermocouple.

Values of the electromotive force E(V) and the temperature T(K) thus measured are converted by the following conversion expression 1 to find an amount of dissolved oxygen (activity of oxygen) within the molten metal:

[Expression 1]

$$a_O = \exp[-\Delta G^\circ/RT] \cdot [(P\theta^{1/4} + \text{Pref}^{1/4}) \exp[-EF/RT] - P\theta^{1/4}]^2$$

where, "$a_O$" is an activity of oxygen within molten metal; "E" is electromotive force (V); "T" is absolute temperature (K); "R" is gas constant; "F" is Faraday constant; "$P\theta$" is partial pressure of oxygen at which ion conduction becomes equal to electron conduction; "Pref" is equilibrium partial pressure of oxygen of a reference substance; and "$\Delta G^\circ$" is change in free energy accompanying to dissolution into molten metal.

Although it is possible to meet with the expectation described above by applying the above-mentioned apparatus for measuring an activity of oxygen within molten metal to the measurement of an activity of oxygen within molten glass, there are still many problems to be solved.

That is, it is necessary to consider a problem peculiar to a molten substance to be measured in developing the applied

2 technology described above. For instance, there is a problem that when the shell is soaked into the molten glass, stabilized zirconia reacts with and eroded by the molten glass, making it difficult to measure continuously for a long period of time. In this regard, although it is preferable to use stabilized zirconia of, a $ZrO_2$-MgO system, a $ZrO_2$-CaO system, a $ZrO_2$-$Y_2O_3$ system, and the like as a zirconia solid electrolyte composing the shell, it has a limit in usable time in terms of corrosion resistance and heat and shock resistance and cannot be used continuously as desired (First Problem).

Further, while the outer electrode has been provided separately from the solid electrolyte as seen in the apparatus for measuring an activity of oxygen within molten metal, there has been a problem when the apparatus thus constructed is used in molten glass that the molten glass between the outer electrode and the solid electrolyte acts as an electrolyte, so that electromotive force varies depending on the size of the outer electrode, a distance between the outer electrode and the solid electrolyte and a positional relationship of the outer electrode and the solid electrolyte with respect to the fluidity of the molten glass. Therefore, the reliability of the measuring accuracy have not been satisfactory (Second Problem).

Further, there has been known a technology of filling mixed powder of Mo-MoO2, of Cr-$Cr_2O_3$, or of Ni-NiO within the end of the shell made of the solid electrolyte in order to form a reference pole in the prior art apparatus for measuring an activity of oxygen within molten metal, such mixed powder is not suitable for the continuous measurement because it tends to be sintered and shrink in high temperature in using the apparatus, causing a gap between the solid electrolyte, and is not stable in the long run (Third Problem).

Further, although an arrangement in which the oxygen activity measuring apparatus is provided also with a temperature measuring apparatus has been adopted in the past because it is also necessary to measure temperature of the molten substance in measuring the activity of oxygen utilizing the solid electrolyte, there has been a problem because of the structure in which they are both provided that not only the apparatus cannot be compact as a whole, but also a pair of thermocouple element wires for the temperature measuring means and a pair of lead wires connected with the outer and inner electrodes for the electromotive force measuring means need to be wired, thus complicating the wiring and hampering the reduction of the cost of the whole apparatus (Fourth Problem).

SUMMARY OF THE INVENTION

According to the first teaching of the present invention, there is provided an apparatus for measuring oxygen within a molten substance That is, in an apparatus for measuring an amount of oxygen within the molten substance to be measured comprising a tubular shell whose one end is closed, which is made of solid electrolyte and which is to be soaked into the molten substance to be measured; a reference pole, provided on an inner face of the tubular shell, for giving a predetermined activity of oxygen; an inner electrode inserted to the reference pole; an outer electrode to be soaked into the molten substance to be measured; and a sheath thermocouple for measuring temperature of the molten substance to be measured; and detecting, by means of the outer electrode and the inner electrode, electromotive force generated between the outer and inner faces of the shell based on a difference of partial pressure of oxygen existing between the molten substance to be measured and the reference pole, the inventive apparatus is provided further with a terminal box, a supporting cylinder extending from the terminal box and an insulating tube made of a porcelain tube extending from the supporting cylinder to form an oxygen probe unit by attaching the tubular shell and the outer electrode at the edge of the insulating tube and by inserting the sheath thermocouple through the insulating tube. The outer electrode is composed of a metal cylinder having a protecting cylinder surrounding the outer periphery of the tubular shell and an opening for exposing the end of the tubular shell. The sheath thermocouple is arranged so as to serve also as the inner electrode by inserting to the tubular shell and by inserting at least the edge of the thermocouple to the reference pole. Temperature measuring means is connected with both element wires of the sheath thermocouple and the electromotive force measuring means is connected with the inner electrode which is served by one element wire of the thermocouple and with the outer electrode via the terminal box.

Further, according to the second teaching of the present invention, the oxygen probe unit is provided with an air supplying port for flowing in air and an air discharge port for discharging the air so as to circulate the air within the terminal box, the supporting cylinder, the insulating tube, and the tubular shell to cool down the unit and to constitute, by the air, a reference substance which gives a predetermined activity of oxygen to the inner face of the tubular shell.

Therefore, according to the present invention, the miniaturized compact oxygen probe unit may be constructed by assembling the tubular shell which is made of the solid electrolyte and whose one end is closed, the sheath thermocouple which is inserted to the shell and which serves also as the inner electrode and the outer electrode which surrounds the outer periphery of the shell to the terminal box.

As described above, according to the present invention, the outer electrode is made from the metal cylinder and is externally fitted to the outer periphery of the shell. The protecting cylinder portion surrounding the outer peripheral face of the shell and an opening for exposing the end of the shell are created by the outer electrode thus formed. Accordingly, because the outer peripheral face of the solid electrolyte is surrounded by the protecting cylinder portion which is formed by the outer electrode itself and the outer peripheral face of the solid electrolyte is protected well from corrosion and thermal shock caused by the molten substance, it becomes possible to provide a measuring apparatus which can be used continuously for a long period of time. Accordingly, the first problem described above may be solved. Meanwhile, because the end of the solid electrolyte is exposed via the opening and contacts with the molten substance to be measured, the measurement of the electromotive force may be carried out favorably by the electromotive force measuring means described above.

Still more, according to the present invention, because the outer electrode made from the metal cylinder is externally fitted to the outer periphery of the shell made of the solid electrolyte and is closely disposed, electromotive force detected between the outer electrode and the inner electrode is always stabilized. In particular, even if the molten substance to be measured is a substance which acts as electrolyte by itself such as molten glass, it is possible to prevent such molten substance which acts as an electrolyte from flowing between the end of the tubular shell and the outer electrode at most, so that the electromotive force may be measured stably and the second problem described above may be solved.

Further, according to the present invention, because the reference pole is constituted by air at the inner face of the shell, it will not shrink like the conventional mixed powder. Accordingly, it is suitable in measuring continuously and stably for a long period of time and thus the third problem described above may be solved.

Further, the present invention allows the integral oxygen probe unit in which the oxygen activity measuring element and the temperature measuring element are assembled to be realized by providing the sheath thermocouple for measuring temperature at the inner face of the end of the shell. Still more, because it is arranged such that one element wire of the thermocouple serves also as the inner electrode as well as its lead wire, the wiring structure is simplified, contributing to the reduction of the cost of the whole apparatus. Accordingly, the fourth problem described above may be solved.

As described above, the oxygen probe unit may be provided with the air supply port for flowing in air and the air discharge port for discharging the air so as to circulate the air within the terminal box, the supporting cylinder, the insulating tube and the tubular shell. It allows the oxygen probe unit to be cooled by the air and the reference substance which gives a predetermined activity of oxygen to the inner face of the tubular shell to be constituted by the air.

Further, according to the present invention, a pair of thermocouple element wires of the sheath thermocouple are provided at the edge connecting portion with an extension which forms a spring section by winding the extension to form a coil configuration. The spring section is caused to elastically contact with the inner face of the tubular shell so that the stable contact between the thermocouple and the shell may be achieved via the spring portion.

The above and other related objects and features of the present invention will be apparent from a reading of the following description of the disclosure found in the accompanying drawings and the novelty thereof pointed out in the appended claims.

BRIEF DESCRIPTION OF DRAWINGS

FIGS. 4a, 4b, and 4c show a manufacturing process of the thermocouple, wherein FIG. 4a is an enlarged view showing a state in which a pair of element wires of the thermocouple are connected at the edge; FIG. 4b is an enlarged view showing a state in which an extension is provided at the portion where the edge of the element wires of the thermocouple is connected; and FIG. 4c is an enlarged view showing a state in which a coiled spring is formed by winding the extension;

DESCRIPTION OF PREFERRED EMBODIMENTS

Preferred embodiments of the present invention will be explained below with reference to the drawings.

Figure 1:
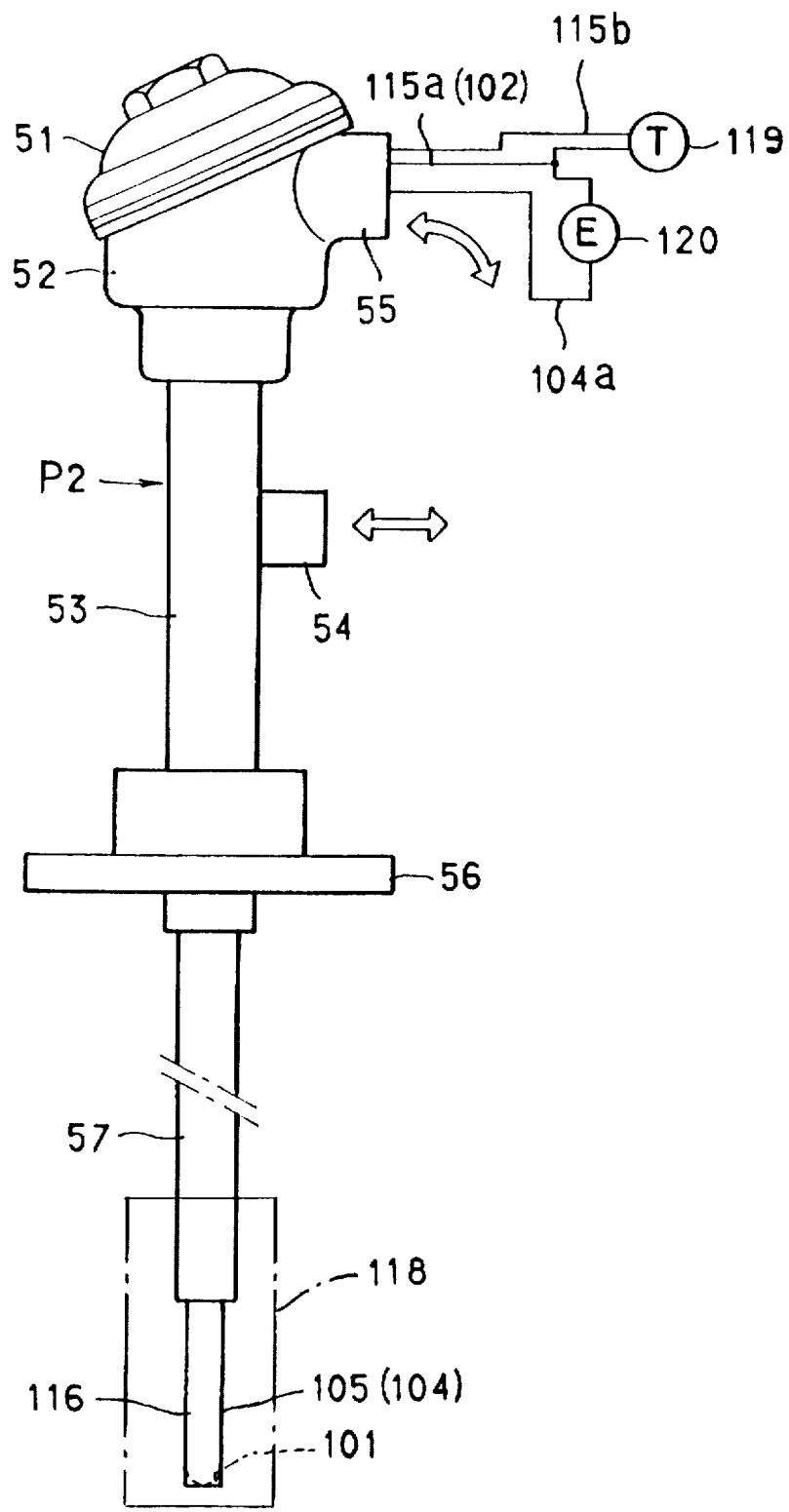
FIG. 1 is a longitudinal section view showing a first embodiment of an oxygen probe unit of an apparatus for measuring oxygen within molten substance based on the present invention.
Figure 2:
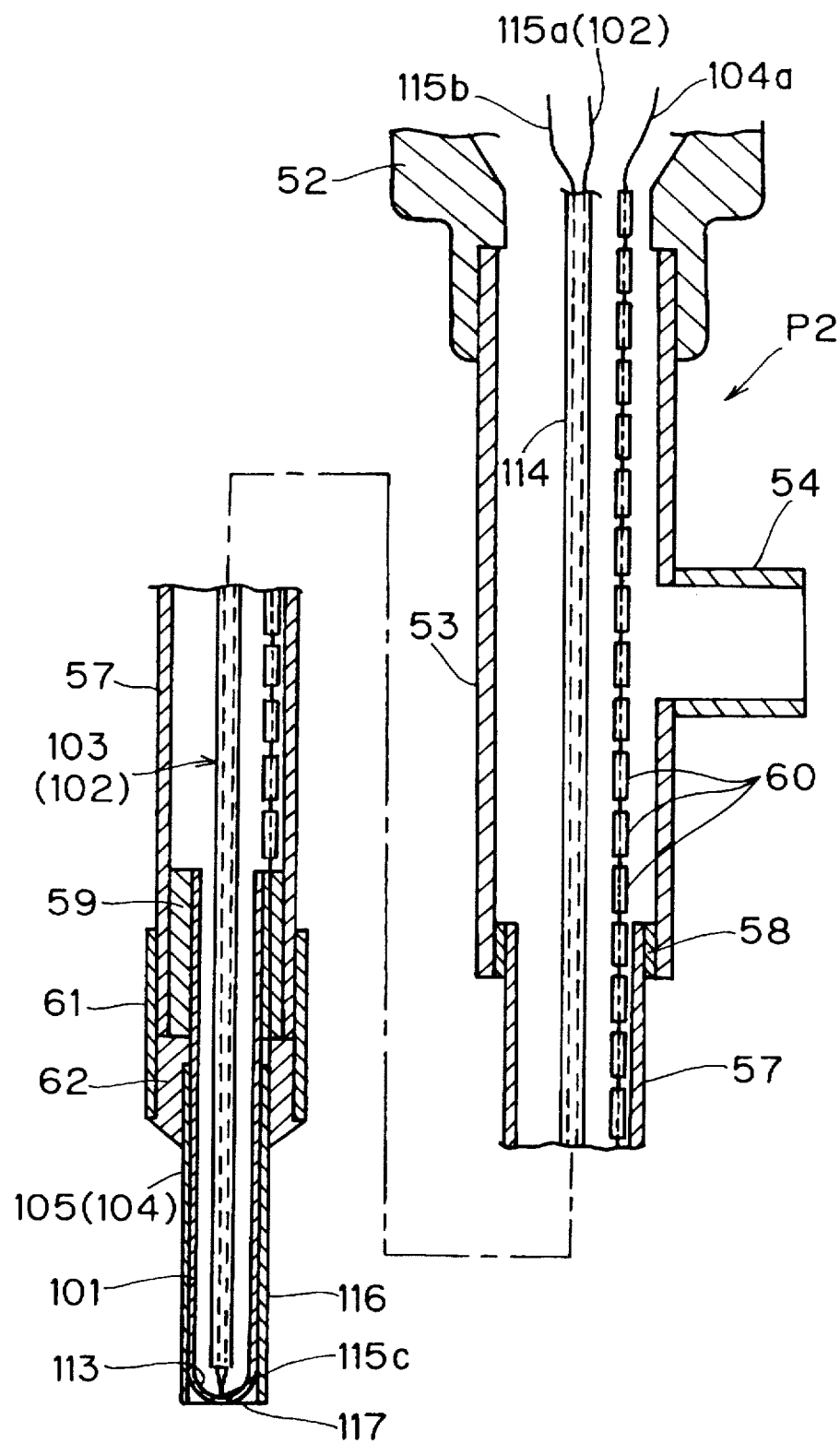
FIG. 2 is an enlarged longitudinal section view of the end portion of the oxygen probe unit of the first embodiment of the present invention.

FIGS. 1 and 2 show an embodiment of the present invention. In an oxygen probe unit P2, a metallic supporting cylinder 53 is extended from a terminal box 52 which is provided with a lid 51 which is openable, an air supply port 54 is provided on the supporting cylinder 53, and an air discharge port 55 which serves also as a port for taking out lead wires is provided on the terminal box 52. Although not shown, air is supplied to the air supply port 54 by air supplying means such as a blower or a compressor and the air is discharged from the air discharge port 55. It is noted that the supply and discharge of air may be arranged in the opposite way. The reference numeral 56 denotes a sliding flange provided around the supporting cylinder 53.

An insulating tube 57 made of an alumina porcelain tube is connected and fixed to the supporting cylinder 53 through an intermediary of fireproofing cement 58 and a connecting cylinder 61 made of an alumina porcelain cylinder is externally fitted around and fixed to the edge of the insulating tube 57 and is preferably secured by fireproofing cement. Further, a tail end of a tubular shell 101 made of solid electrolyte is internally fitted into the edge of the insulating tube 57 and is secured by fireproofing cement 59.

A metal cylinder 105 is externally fitted around and secured to the tubular shell 101 made of solid electrolyte. The metal cylinder 105 is made of Mo, Fe, Pt, or the like and serves also as an outer electrode 104. A tail end of the metal cylinder 105 is inserted to the connecting cylinder 61 together with the tubular shell 101 and is secured by fireproofing cement 62. It is noted that it is preferable to form the outer electrode 104 by Pt when it is intended to measure an activity of oxygen within molten glass by the present invention. By the way, because the outer electrode 104 is provided at the edge of the insulating tube 57 via the connecting cylinder 61, the whole length of the outer electrode 104 may be shortened, allowing to suppress the cost to the minimum even if it is made of platinum which is expensive.

The tubular shell 101 is formed in a body into the shape of tube whose end is closed semispherically by solid electrolyte. While the solid electrolyte may be selected from various zirconia solid electrolytes, it is preferable to use a $ZrO_2$-MgO system, a $ZrO_2$-CaO system, $ZrO_2$-$Y_2O_3$ system, or their compound stable type system (e.g. $ZrO_2$-MgO-CaO system) when it is intended to measure an activity of oxygen within the molten glass by the present invention. It is preferable to select stabilized zirconia of the MgO system if corrosion resistance and heat and shock resistance to the molten glass is to be considered. The outer periphery of the tubular shell 101 is surrounded by a protecting cylinder section 116 and the end of the tubular shell 101 is exposed from an end opening 117 of the metal cylinder 105.

A reference pole 113 made of a reference substance which gives a predetermined activity of oxygen is provided at the inner face of the tubular shell 101. Although the reference pole 113 may be formed by mixed powder of Fe, Ni, Cr, or Mo and powder of their oxides filled within the tubular shell, or of air, CO gas, or the like, it is preferable to form it by air supplied from an air supply port 54 as shown in the figure in view of the stability in a long period of time and the stabilization of the activity of oxygen as described above.

A sheath thermocouple 103 which serves also as an inner electrode 102 is inserted through the supporting cylinder 53 and the insulating tube 57, and the edge of the sheath thermocouple 103 is inserted to the tubular shell 101. The sheath thermocouple 103 comprises a protecting tube 114 made of porcelain and thermocouples 115a and 115b inserted within the protecting tube 114. A temperature contact 115c which projects out of the edge of the protecting tube 114 contacts with the inner face of the closed end of the tubular shell 101.

Figure 3:
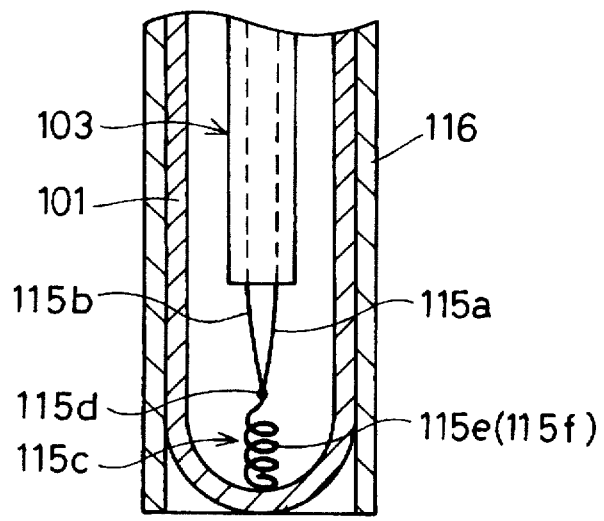
FIG. 3 is an enlarged longitudinal section view of an edge portion of the oxygen probe unit according to the embodiment of the present invention.

In the illustration, R-thermocouple in which the element wire 115a on the minus pole side is made of platinum and the element wire 115b on the plus side is made of an alloy of platinum and rhodium is used as the thermocouple. Those element wires 115a and 115b are taken out of the protecting tube 114 and their extension ends are connected to a terminal block of the terminal box 52 and are then connected to temperature measuring means 119 via lead wires taken out of the lead takeout port 55 which serves also as the air discharge port. It is noted that the element wire 115a on the minus pole side serves also as the inner electrode 102. As shown in FIG. 3, an extension 115e is connected to an edge connecting portion 115d where the thermocouples 115a and 115b are connected to each other and is wound like a coil to form a spring section 115f. The spring 115f is caused to elastically contact with the inner face of the closed end of the tubular shell 101. The temperature contact section 115c is thus formed by the spring section 115f. That is, the spring portion 115f is caused to elastically contact with the inner face of the tubular shell 101 while being slightly compressed to form the temperature contact section 115c which contacts favorably with the tubular shell 101.

Figure 4A:
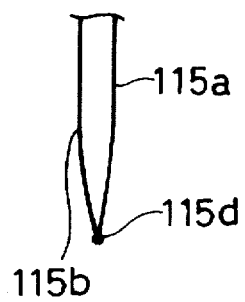
Figure 4B:
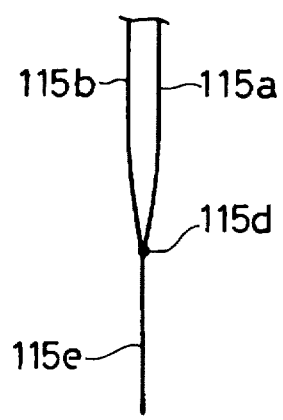
Figure 4C:
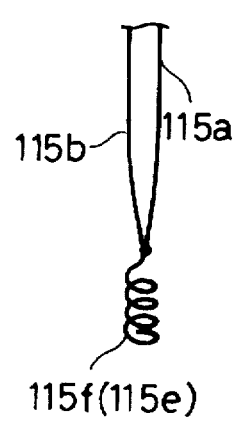

FIGS. 4a through 4c show a method for fabricating the temperature contact section 115c having such spring portion 115f. As shown in FIG. 4a, the R thermocouple described above is arranged such that both edges of the element wire 115a made of platinum and the element wire 115b made of an alloy of platinum and rhodium are connected each other at the connecting portion 115d. This point is no different from the known thermocouple. Then, in the present invention, the extension 115e made of platinum is connected to the connecting portion 115d as shown in FIG. 4b. This connection is made by welding the end of the extension 115e to the connecting portion 115d. Next, the extension 115e is wound around a core such as a rod not shown and the core is then pulled out to form the coiled spring 115f as shown in FIG. 4c.

An outer electrode lead wire 104a made of platinum is connected to the outer electrode 104. Preferably, its connecting part is buried into and coated by fireproofing cements 59 and 62 described above. This outer electrode lead wire 104a is protected from heat by inserting through a number of short insulating protecting tubes 60 between the outer electrode 104 and the terminal box 52. The extension end of the lead wire 104a is connected to the terminal block and is then connected to electromotive force measuring means 120 via a lead wire taken out of the air discharge takeout port 55. That is, the electromotive force measuring means 120 is connected to the outer electrode lead wire 104a and the inner electrode 102, which serves also as the wire 115a on the minus pole side of the thermocouple as described above, via the lead wires.

The oxygen probe unit P2 constructed as described above is suitable for measuring oxygen in a molten substance to be measured such as molten glass in particular. In measuring an activity of oxygen within the molten glass, a measuring section 118 (shown by a dashed line in FIG. 1) of the oxygen probe unit P2 is soaked into the molten glass while suspending it by the sliding flange 56. Then, electromotive force E(V) is generated between the inner and outer faces of the tubular shell 101 made of the solid electrolyte based on a difference of partial pressure of oxygen existing between the molten glass and the reference pole 113 and is measured by the electromotive force measuring means 120 via the inner electrode 102 and the outer electrode 104. Further, the sheath thermocouple 103 detects temperature T(K) of the molten glass via the edge of the tubular shell 101 and the temperature measuring means 119 measures this temperature T(K). Values of the electromotive force E(V) and the temperature T(K) are converted by the conversion expression as shown in Expression 1 to find an amount of dissolved oxygen (activity of oxygen "$a_o$") within the molten glass.

At this time, the air supplied from the air supply port 54 of the supporting cylinder 53 and discharged from the air discharge port 55 of the terminal box 52 is circulated within the tubular shell 101 via the insulating tube 57 to, thereby, form the reference pole 113 which gives an activity of oxygen stably to the inner face of the edge of the tubular shell 101. In the same time, the circulating air cools not only the tubular shell 101 itself but also the supporting cylinder 53 and the insulating tube 57. It also cools the insulating tube 114 through which the element wires 115a and 115b of the thermocouple are inserted as well as the insulating protecting tube 60 through which the outer electrode lead wire 104a is inserted.

|Comparative Case|

Figure 5:
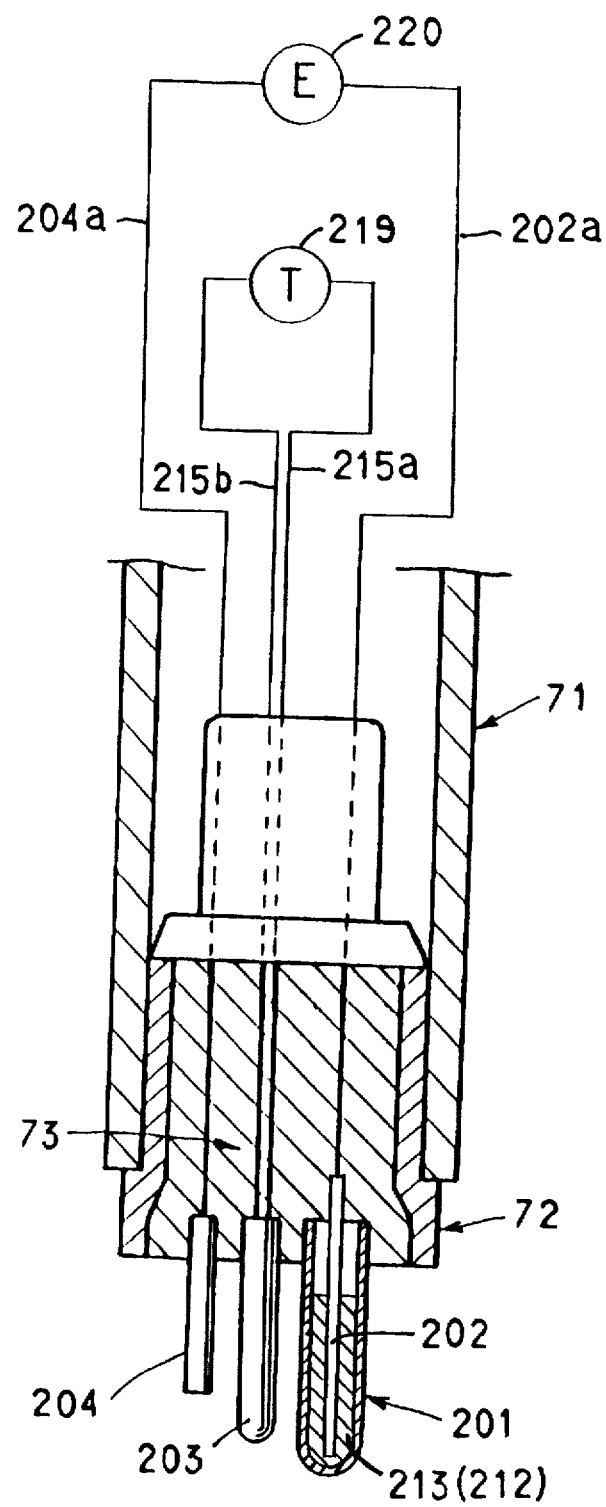
FIG. 5 is a longitudinal section view showing the prior art.

FIG. 5 shows a prior art apparatus in which fireproofing cement 73 is filled in a housing 72 whose edge is opened and which is attached to a holding cylinder 71 made of a paper tube. A tubular shell 201 made of solid electrolyte, a sheath thermocouple 203, and an outer electrode 204 formed by a rod of Mo are supported by the fireproofing cement 73 by embedding each tail end thereto while projecting each edge out of the housing 72.

A reference substance 212 made of a mixture of metal powder and powder of oxide of the metal is filled in the tubular shell 201. The reference substance 212 constitutes a reference pole 213 which gives a predetermined activity of oxygen to the inner face of the tubular shell 201 and an inner electrode 202 formed by a rod of Mo is embedded and inserted through the reference substance 212.

In such prior art apparatus, element wires 215a and 215b of the sheath thermocouple 203 are connected to temperature measuring means 219 and a lead wire 204a of the outer electrode 204 and a lead wire 202a of the inner electrode 202 are connected to electromotive force measuring means 220. Accordingly, the wiring requires the four wires.

Then, it may be understood that the prior art apparatus requires a large number of parts and becomes large as compared to the present invention described above, disallowing to obtain a compact apparatus.

By the way, when oxygen within a molten substance is measured by using the prior art apparatus, the tubular shell 201 which is made of solid electrolyte may crack or the like and be damaged by thermal shock when the housing 72 is soaked into the molten substance.

Further, when the molten substance to be measured is molten glass, zirconia solid electrolyte which makes the tubular shell 201 reacts with the molten glass and is corroded, thus making it difficult to measure continuously for a long period of time. Further, because the molten glass acts as an electrolyte between the outer electrode 204 and the tubular shell 201 which are disposed separately from each other, the electromotive force becomes unstable.

As compared to that, it may be readily understood that the present invention eliminates the disadvantages of the prior art completely and exhibits excellent effects.

While preferred embodiments have been described, variations thereto will occur to those skilled in the art within the scope of the present inventive concepts which are delineated by the following claims.

What is claimed is:

1. An apparatus for measuring oxygen within a molten substance, comprising:

a tubular shell whose one end is closed, which is made of solid electrolyte and which is to be soaked into the molten substance;

a reference pole, provided within an inner face of an end of said shell, for giving a predetermined activity of oxygen;

an inner electrode inserted to said reference pole;

an outer electrode which is to be soaked into the molten substance; and a sheath thermocouple for measuring temperature of the molten substance;

said apparatus measuring an amount of oxygen within the molten substance by detecting, by means of said outer electrode and said inner electrode, electromotive force generated between the outer and inner faces of said tubular shell based on a difference of partial pressure of oxygen existing between the molten substance and said reference pole;

said apparatus further comprising a terminal box, a supporting cylinder extending from said terminal box, and an insulating tube made of a procelain tube extending from said supporting cylinder to form an oxygen probe unit by attaching said tubular shell and said outer electrode at the edge of said insulating tube and by inserting said sheath thermocouple through said tubular shell;

said outer electrode being composed of a metal cylinder having a protecting cylinder portion surrounding the outer periphery of said tubular shell and an opening for exposing the end of said tubular shell;

said sheath thermocouple being arranged so as to serve also as said inner electrode by inserting through said tubular shell and by inserting at least the edge of said thermocouple to the reference pole; and temperature measuring means being connected with both element wires of said sheath thermocouple and electromotive force measuring means being connected with said inner electrode which is served by one element wire of said thermocouple and with said outer electrode via said terminal box.

2. The apparatus for measuring oxygen within a molten substance according to claim 1, wherein said tubular shell is made of stabilized zirconia selected among a $ZrO_2$-MgO system, a $ZrO_2$-CaO system, and a $ZrO_2$-$Y_2O_3$ system.

3. The apparatus for measuring oxygen within a molten substance according to claim 1, wherein said metal cylinder which composes said outer electrode is made of Pt so as to measure an activity of oxygen within molten glass.

4. The apparatus for measuring oxygen within a molten substance according to claim 1, wherein said insulating tube to which said tubular shell and said outer electrode are attached is made from an alumina porcelain tube.

5. The apparatus for measuring oxygen within a molten substance according to claim 1, wherein the reference substance composing said reference pole of said tubular shell is selected from air or CO gas.

6. The apparatus for measuring oxygen within a molten substance according to claim 1, wherein said thermocouple element wires of said sheath thermocouple is provided with an extension at the edge connecting portion of said both element wires, a spring section is formed by winding said extension like a coil and said spring section is caused to elastically contact with the inner face of said tubular shell.

7. An apparatus for measuring oxygen within a molten substance, comprising:

a tubular shell whose one end is closed, which is made of solid electrolyte and which is to be soaked into the molten substance;

a reference pole, provided within an inner face of an end of said shell, for giving a predetermined activity of oxygen;

an inner electrode inserted to said reference pole;

an outer electrode which is to be soaked into the molten substance; and a sheath thermocouple for measuring temperature of the molten substance;

said apparatus measuring an amount of oxygen within the molten substance by detecting, by means of said outer electrode and said inner electrode, electromotive force generated between the outer and inner faces of said tubular shell based on a difference of partial pressure of oxygen existing between the molten substance and said reference pole;

said apparatus further comprising a terminal box, a supporting cylinder extending from said terminal box, and an insulating tube made of a porcelain tube extending from said supporting cylinder to form an oxygen probe unit by attaching said tubular shell and said outer electrode at the edge of said insulating tube and by inserting said sheath thermocouple through said tubular shell;

said outer electrode being composed of a metal cylinder having a protecting cylinder surrounding the outer periphery of said tubular shell and an opening at the end of the metal cylinder for exposing the end of said tubular shell;

said sheath thermocouple being arranged so as to serve also as said inner electrode by inserting through said tubular shell and by inserting at least the edge of said thermocouple to the reference pole;

said oxygen probe unit being provided with an air supplying port for flowing in air and an air discharge port for discharging the air to circulate the air within said terminal box, said supporting cylinder, said insulating tube, and said tubular shell to cool down said unit and to constitute, by the air, a reference substance which gives a predetermined activity of oxygen to the inner face of said tubular shell.

8. The apparatus for measuring oxygen within a molten substance according to claim 7, the thermocouple element wires of said sheath thermocouple compose an R thermocouple provided with the element wire made of platinum and the element wire made of an alloy of platinum and rhodium, an extension is provided at the edge connecting portion of said both element wires, a spring section is formed by winding said extension like a coil and said spring section is caused to elastically contact with the inner face of said tubular shell.

* * * * *